United States Patent
Lan et al.

(10) Patent No.: US 11,655,204 B2
(45) Date of Patent: May 23, 2023

(54) PROMOTOR AND METHOD FOR PREPARING THE SAME

(71) Applicant: NATIONAL CHUNG SHAN INSTITUTE OF SCIENCE AND TECHNOLOGY, Taoyuan (TW)

(72) Inventors: Yi-Kang Lan, Taoyuan (TW); Chi-Wi Ong, Taoyuan (TW); Yong-Yun Zhang, Taoyuan (TW)

(73) Assignee: NATIONAL CHUNG SHAN INSTITUTE OF SCIENCE AND TECHNOLOGY, Taoyuan (TW)

( * ) Notice: Subject to any disclaimer, the term of this patent is extended or adjusted under 35 U.S.C. 154(b) by 27 days.

(21) Appl. No.: 17/180,848

(22) Filed: Feb. 21, 2021

(65) Prior Publication Data
US 2022/0267250 A1    Aug. 25, 2022

(51) Int. Cl.
C07C 211/46    (2006.01)
C07C 211/52    (2006.01)
C08F 4/34      (2006.01)
C07C 209/68    (2006.01)

(52) U.S. Cl.
CPC .......... *C07C 211/46* (2013.01); *C07C 209/68* (2013.01); *C07C 211/52* (2013.01); *C08F 4/34* (2013.01); *C07C 2601/16* (2017.05)

(58) Field of Classification Search
None
See application file for complete search history.

(56) References Cited

PUBLICATIONS

Rao et al. (Arkivoc (Gainesville, FL, United States) (2004), (1), 88-100, Coden: Agfuar, URL: http://www.arkat-usa.org/ark/journal/2004/General_Part(i)/04-1105D/1105D.) (Year: 2004).*

* cited by examiner

*Primary Examiner* — Sudhakar Katakam
*Assistant Examiner* — Jennifer C Sawyer

(57) ABSTRACT

A novel promotor which contains an aniline derivative is introduced. By using the promotor alone, the time and temperature of the curing reaction of the vinyl ester resin can be controlled by the unique steric effect and electronic properties of the aniline derivative. A method for preparing the above promotor is also introduced.

1 Claim, 7 Drawing Sheets

BPO 3g DMA 1.2g

BPO 3g N-Ipr-N-Meaniline 1.4774g

BPO 3g N,N-diisopropylaniline 1.755g

PROMOTOR AND METHOD FOR PREPARING THE SAME

BACKGROUND OF THE INVENTION

1. Field of the Invention

The present disclosure relates to a promotor and a method for preparing the same, and in particular to a promotor for controlling the time and temperature of the curing reaction for forming vinyl ester resin and a method for preparing the same.

2. Description of the Related Art

International unsaturated polyester/vinyl ester market and applications are concentrated in building materials and transportation/ships, with an output value of 1.5 billion US dollars in 2014. The domestic market is distributed in pouring, rubber shell, soil filling, buttons, FRP, ships, winding, decorative panels, artificial stone and SMC/BMC, etc. Both types of resins need to be initiated by adding hardeners and promotors during curing and molding, but if large/thick-shell workpieces are to be poured, the heat release and reaction speed of the curing reaction must be controlled.

The curing of vinyl ester resin is generally guided by the peroxide curing agent MEKPO and cobalt salt. The peroxide first reacts with cobalt to generate free radicals, and then the free radicals undergo free radical polymerization with the double bonds in the vinyl ester. The curing agent generally used is organic peroxide such as MEKPO, and the promotor used is generally the cobalt salt, in which cobalt octoate and cobalt oxalate are commonly used.

In the curing of vinyl esters, initiators and promotors must be used, and then the reaction solvent, i.e. styrene, and vinyl ester monomers are crosslinked into the network structure (curing) by using the free radical reaction. Two kinds of the most commonly used organic peroxides, Methyl Ethyl Ketone Peroxide (MEKPO) and Bezoyl peroxide (BPO), can both be used as the initiators, and since the free radical reaction will be accompanied by a large amount of heat release, heat will accumulate when the workpiece is too large, resulting in defects and failure.

The previous technology is to coat fibers with resin, and then completes the preparation of composite materials through curing of the resin. For the curing of the resin, this technology only uses the ratio of retarder or curing agent to control the time when the curing starts. However, the curing of vinyl esters uses free radical reaction to carry out the crosslinking, the reaction speed thereof is fast and a large amount of reaction heat is released; once curing starts, the temperature will rise sharply, and the temperature change rate will deviate from the control of the ratio of retarder or curing agent. Thus, the previous technology cannot improve the problem of too fast temperature change.

Therefore, the industry currently needs the chemical substance or method for controlling the exothermic temperature and reaction rate of the whole vinyl ester curing reaction in order to control the quality of the vinyl ester workpiece.

BRIEF SUMMARY OF THE INVENTION

In view of the shortcomings of the above-mentioned conventional technology, a main object of the present invention is to form a new type of promotor by adjusting the electron and steric effects of the substituents on the promotor to control the kinetics of free radical generation and curing temperature in the vinyl ester curing reaction under the presence of the peroxides.

Another object of the present invention is to provide a novel promotor for controlling the free-radical polymerization of the vinyl ester system. The novel promotor can control the heat release and rate of radical polymerization of the vinyl ester system in the presence of peroxide as well as in the presence or absence of the polymer inhibitor.

To achieve the above object, according to one aspect proposed by the present invention, a promotor is provided. The promotor includes an aniline derivative, which has a structure of formula (I):

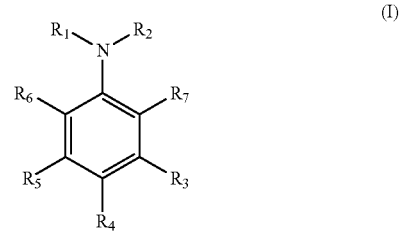

wherein $R_1$ is an alkyl group or a cycloalkyl group; $R_2$ is an alkyl group or a cycloalkyl group; $R_3$, $R_4$, $R_5$, $R_6$ and $R_7$ are individually one of hydrogen, an electron withdrawing group and an electron pushing group, wherein the electron withdrawing group and the electron pushing group do not exist in $R_3$, $R_4$, $R_5$, $R_6$ and $R_7$ at the same time. In the promotor described above, the aniline derivative has the following structures:

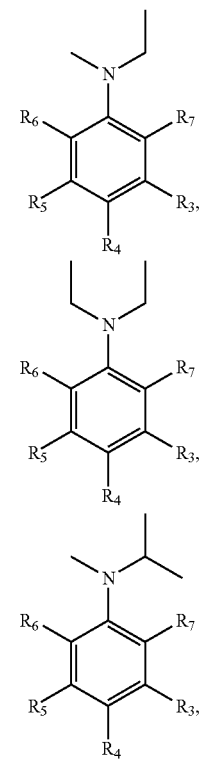

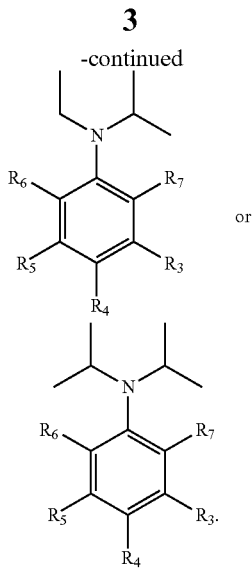

In the promotor described above, in the aniline derivative, the alkyl group is selected from the group consisting of methyl, ethyl, propyl, isopropyl, butyl, di-sec-butyl and tert-butyl, and the cycloalkyl group is selected from the group consisting of pyrrolidinyl, piperidinyl, cyclopentane and cyclohexane.

In the promotor described above, in the aniline derivative, the electron withdrawing group is selected from the group consisting of $NO_2$, CN, F, COOH, Cl, Br and I.

In the promotor described above, in the aniline derivative, the electron pushing group is selected from the group consisting of $(CH_3)_3C$, $(CH_3)_2CH$ and $CH_3CH_2$.

The present invention also provides a method for preparing a promotor, wherein the promotor comprises an aniline derivative having the following structure:

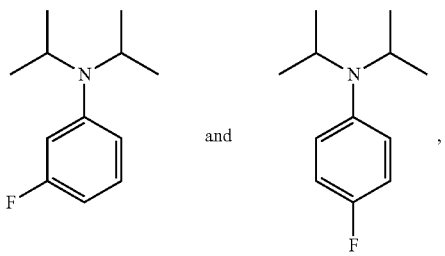

and the method comprises the following steps:

(a) pouring bromofluorobenzene and isopropylamine into a bottle and slowly adding potassium tert-butoxide to form a mixture;

(b) heating the mixture obtained in step (a) to reflux, and then filtering the mixture to remove potassium tert-butoxide after cooling to room temperature to obtain a first liquid;

(c) removing isopropylamine and tert-butanol from the first liquid obtained in step (b) by distillation under reduced pressure to form a second liquid; and (d) obtaining an organic phase from the second liquid obtained in step (c) by stratification, adding water into the organic phase for extraction and washing until the organic phase is not turbid, drying the organic phase with anhydrous magnesium sulfate and then filtering, removing excess solvent by concentration under reduced pressure, and finally removing excess reactant bromofluorobenzene from the concentrated organic phase by vacuum distillation to obtain the promotor.

The present invention further provides a polymerization initiation system for thermosetting resin, including a peroxide initiator and the promotor of formula (I).

In the polymerization initiation system for thermosetting resin described above, the thermosetting resin is vinyl ester resin, and the peroxide initiator is benzyl peroxide.

The novel promotor of the present invention can control the free radical reaction mechanism, such that the whole curing reaction of the vinyl ester resin can be controlled below 160° C. and the reaction time thereof is not more than 100 minutes to improve the shortcomings of defect and failure resulted from the accumulation of heat when the workpiece is too large.

The above summary, the following detailed description and drawings are all for the purpose of further explaining the methods, means and effects adopted by the present invention for achieving the intended purpose. Other objects and advantages of the present invention will be described in the following description and drawings.

DETAILED DESCRIPTION OF THE INVENTION

To facilitate understanding of the object, characteristics and effects of this present disclosure, embodiments together with the attached drawings for the detailed description of the present disclosure are provided.

A novel promotor of the present invention contains an aniline derivative. By using the promotor alone, the time and temperature of the curing reaction of the vinyl ester resin can be controlled by the unique steric effect and electronic properties of the aniline derivative.

The present invention provides a promotor. The promotor includes an aniline derivative, which has a structure of formula (I):

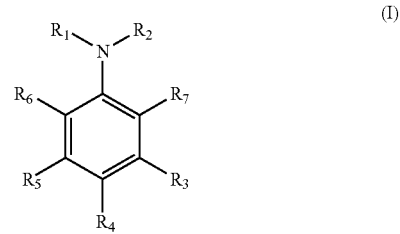

wherein $R_1$ is an alkyl group or a cycloalkyl group; $R_2$ is an alkyl group or a cycloalkyl group; $R_3$, $R_4$, $R_5$, $R_6$ and $R_7$ are individually one of hydrogen, an electron withdrawing group and an electron pushing group, wherein the electron withdrawing group and the electron pushing group do not exist in $R_3$, $R_4$, $R_5$, $R_6$ and $R_7$ at the same time.

Figure 1:
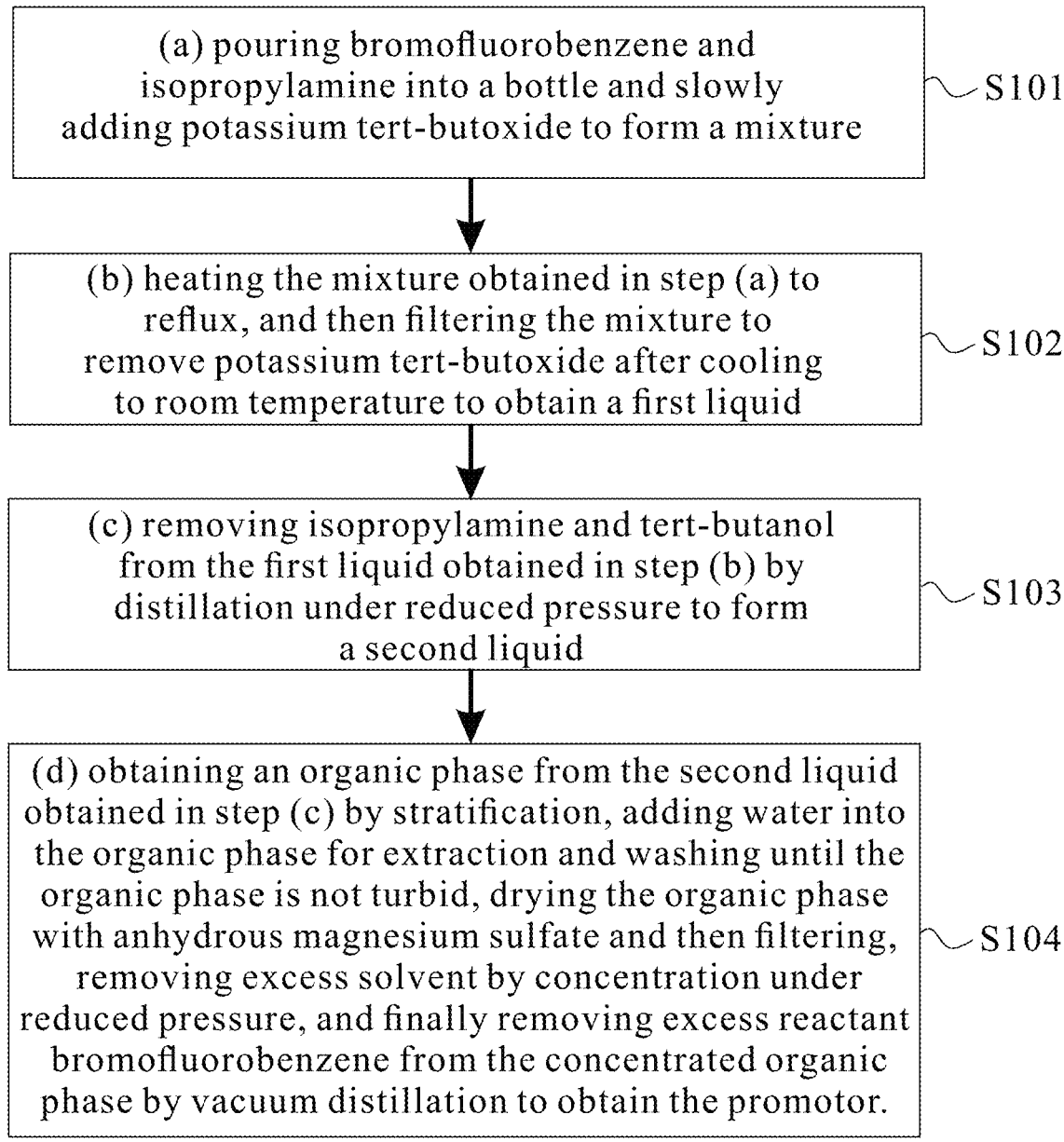
FIG. 1 is a flow chart showing a method for preparing the promotor of the present invention.

With reference to FIG. 1, which is a flow chart showing a method for preparing the promotor of the present invention. The method comprises the following steps: (a) pouring bromofluorobenzene and isopropylamine into a bottle and slowly adding potassium tert-butoxide to form a mixture; (b) heating the mixture obtained in step (a) to reflux, and then filtering the mixture to remove potassium tert-butoxide after cooling to room temperature to obtain a first liquid; (c) removing isopropylamine and tert-butanol from the first liquid obtained in step (b) by distillation under reduced pressure to form a second liquid; and (d) obtaining an organic phase from the second liquid obtained in step (c) by stratification adding water into the organic phase for extraction and washing until the organic phase is not turbid, drying the organic phase with anhydrous magnesium sulfate and then filtering, removing excess solvent by concentration under reduced pressure, and finally removing excess reactant bromofluorobenzene from the concentrated organic phase by vacuum distillation to obtain the promotor.

The promotor prepared by the present invention may comprises the aniline derivative having the following structures:

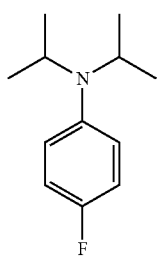 and 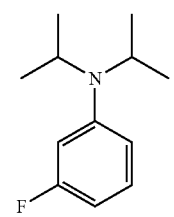

Generally, when BPO is used as a radical polymerization initiator, the reaction temperature is about 60-80° C. to promote homolytic cleavage of the O-O bond of BPO to generate free radicals. When the promotor is added to the reaction system, the redox reaction can be carried out at low temperature to generate free radicals, and the polymer polymerization reaction can be carried out at room temperature.

From the reaction mechanism of BPO and DMA promotor, it can be speculated that the substituent steric effect of the amino group of the promotor is sufficient to affect the rate of the polymerization reaction. Therefore, we design and synthesize new promotors with different steric hindrance/electronic effects, N-Ethyl-N-methylaniline (I-a), N,N-diethylaniline (DEA) (I-b), N-isopropyl-N-methylaniline (I-c), N-ethyl-N-isopropylaniline (I-d), N,N-diisopropylaniline (I-e), para-N,N-diisopropylfluoroaniline (I-f) and meta-N,N-diisopropylfluoroaniline (I-g):

(I-a)

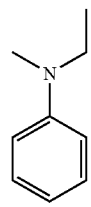

(I-b)

(I-c)

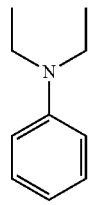

(I-d)

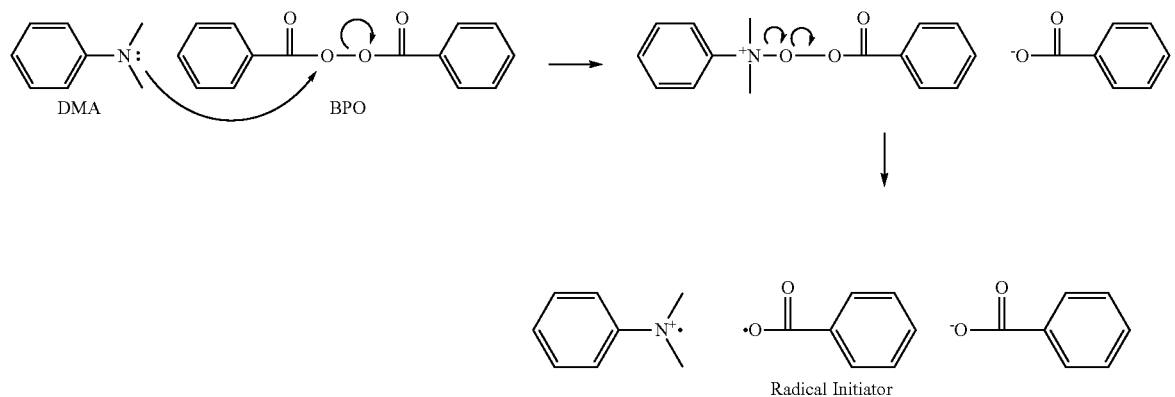

Radical Initiator

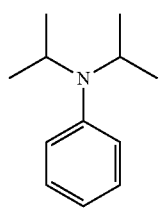
(I-e)

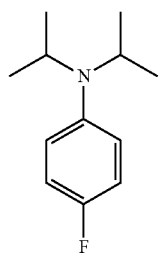
(I-f)

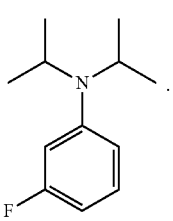
(I-g)

In general, the radical in vinyl ester polymerization is generated by the added peroxide (BPO in this example) and the initiator (DMA in this example). Since the substituent steric effect of the amino group of the promotor is sufficient to affect the rate of the polymerization reaction, different sterically hindered substituent promoters of formulas (I-a), (I-b), (I-c), (I-d), (I-e), (I-f), (I-g) are synthesized and observed for their effects on the polymerization rate and reaction temperature.

the reaction was finished, extraction was carried out three times with the aqueous sodium hydroxide solution and dichloromethane. The organic phase was taken and dewatered with anhydrous magnesium sulfate, concentrated under reduced pressure to remove dichloromethane, and then subjected to column chromatography (SiO₂ 0.045-0.075 mm, EA/Hexane=1: 40).

Example 2 Synthesis of N,N-diethylaniline (I-b): Aniline (10 g, 1 equivalent) and 2.2 equivalents of bromoethane were added into a 150 ml round-necked flask under nitrogen atmosphere and heated to reflux for 8 hours. After the reaction was finished, extraction was carried out three times with the aqueous sodium hydroxide solution and dichloromethane. The organic phase was taken and dewatered with anhydrous magnesium sulfate, concentrated under reduced pressure to remove dichloromethane, and then subjected to column chromatography (SiO₂ 0.045-0.075 mm, EA/Hexane=1: 25).

Example 3 Synthesis of N-iPr-N-Meaniline (I-c): N-methylaniline (10 g, 1 equivalent) and 1.2 equivalents of 2-bromopropane were added into a 150 ml round-necked flask under nitrogen atmosphere and heated to reflux for 8 hours. After the reaction was finished, extraction was carried out three times with the aqueous sodium hydroxide solution and dichloromethane. The organic phase was taken and dewatered with anhydrous magnesium sulfate, concentrated under reduced pressure to remove dichloromethane, and then subjected to column chromatography (SiO₂ 0.045-0.075 mm, EA/Hexane=1: 40).

Example 4 Synthesis of N-ethyl-N-isopropylaniline (I-d): N-ethylaniline (10 g, 1 equivalent) and 1.2 equivalents of 2-bromopropane were added into a 150 ml round-necked flask under nitrogen atmosphere and heated to reflux for 18 hours. After the reaction was finished, extraction was carried out three times with the aqueous sodium hydroxide solution and dichloromethane. The organic phase was taken and dewatered with anhydrous magnesium sulfate, concentrated under reduced pressure to remove dichloromethane, and

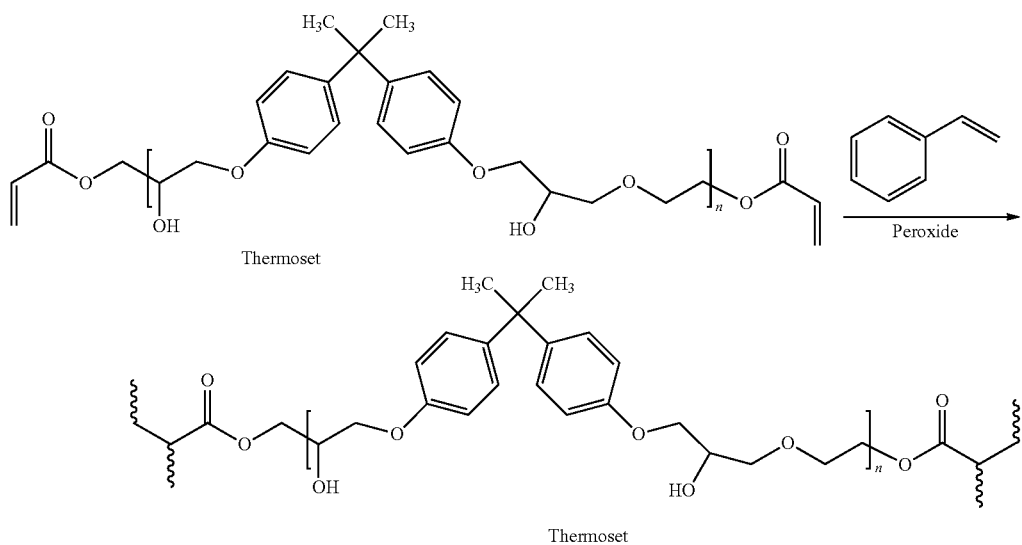

Example 1 Synthesis of N-Et-N-Meaniline (I-a): N-methylaniline (10 g, 1 equivalent) and 1.2 equivalents of bromoethane were added into a 150 ml round-necked flask under nitrogen atmosphere and heated to reflux for 8 hours. After then subjected to column chromatography (SiO₂ 0.045-0.075 mm, EA/Hexane=1: 40).

Example 5 Synthesis of N-diisopropylaniline (I-e): Bromobenzene (22.5 g, 1 equivalent), 4 equivalents of diisopropylamide and 2.8 equivalents of potassium tert-butoxide were added into a 250 ml round-necked flask under nitrogen atmosphere and heated to reflux for 2-3 days. After the reaction was finished, the unreacted diisopropylamide was removed by concentration under reduced pressure, and then neutralization was carried out with aqueous hydrogen chloride solution. After extraction was carried out three times with ether, the water layer was taken and alkalized with aqueous sodium hydroxide solution, and then extraction was carried out three times with ether. The organic phase was taken, dewatered with anhydrous magnesium sulfate and concentrated under reduced pressure to remove ether, and then the product was obtained.

Example 6 Synthesis of para-N,N-diisopropylfluoroaniline (I-f) and meta-N,N-diisopropylfluoroaniline (I-g): Bromofluorobenzene, potassium tert-butoxide and isopropylamine were used to prepare a 1:1 mixture of meta-N,N-diisopropylfluoroaniline and para-N,N-diisopropylfluoroaniline. 70 mL of 4-bromofluorobenzene and 360 mL of diisopropylamine were poured into the bottle, stirred with slow addition of 200 g t-buOK, and then heated to reflux at 140~150° C. When the reaction solution was cooled to room temperature, filtration was carried out to remove t-buOK, and then the filtered liquid was distilled under reduced pressure to take out diisopropylamine and tBuOH. At this time, the bottle appeared to be stratified. The organic phase was taken and washed by extraction with water until the organic phase was not turbid. Afterwards, the organic phase was dried with anhydrous magnesium sulfate, filtered, and concentrated under reduced pressure to remove excess solvent. Finally, the concentrated organic phase was distilled under vacuum to remove the excess reactant 4-bromofluorobenzene to obtain the mixture of meta-N,N-diisopropylfluoroaniline (I-g) and para-N,N-diisopropylfluoroaniline (I-f).

Example 8: 150 g of vinyl ester (Mono) and 3 g of BPO were added respectively to the promotors listed in the table below to perform the curing of vinyl ester, and the impact of various promotors with sterically hindered substituent on the polymerization rate and reaction temperature were observed.

TABLE 1

Addition amount of promotors for curing of vinyl ester

| Promotors | Weight |
|---|---|
| DMA | 1.2 g |
| N—Et—N-Meaniline (I-a) | 1.33 g |
| DEA (I-b) | 1.47 g |
| N—iPr—N-Meaniline (I-c) | 1.47 g |
| N—Et—N-iPraniline (I-d) | 1.61 g |
| N,N-diisopropoylaniline (I-e) | 1.75 g |

Figure 2:
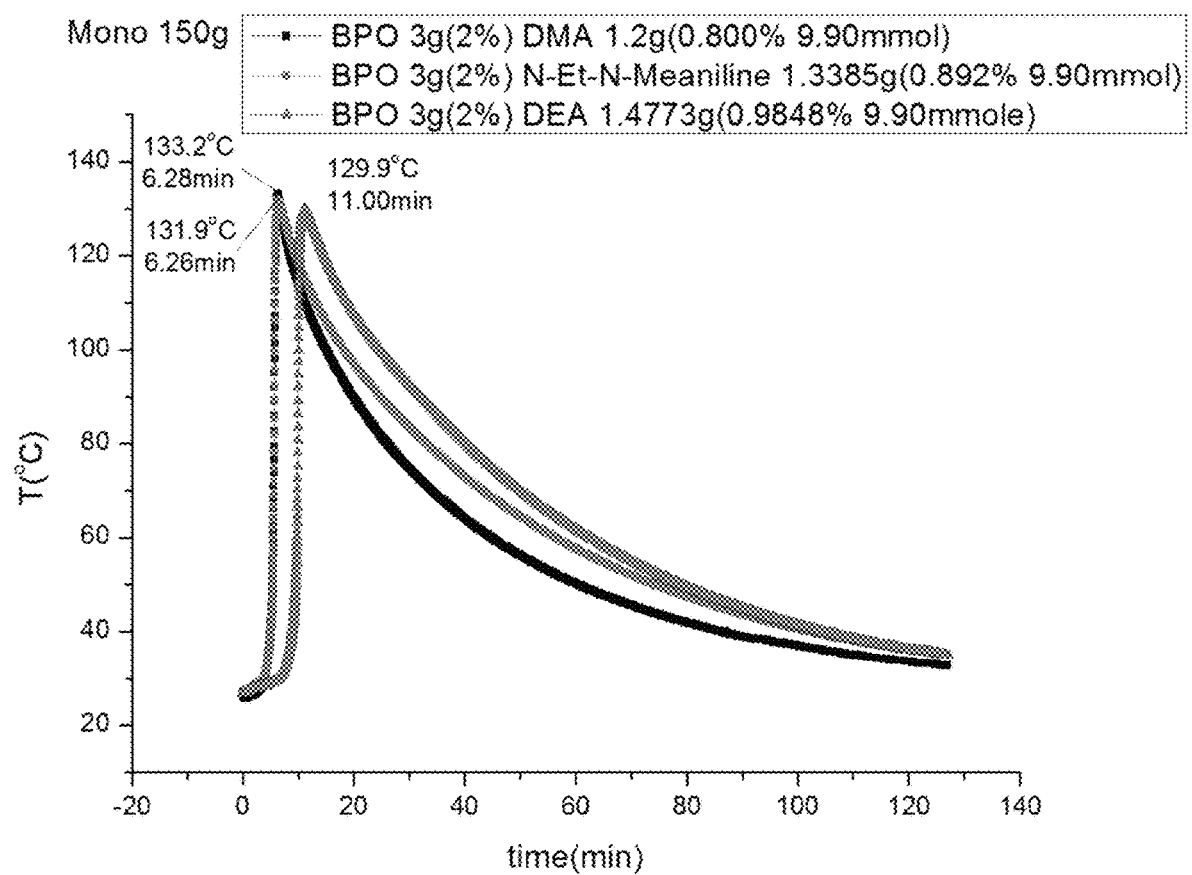
FIG. 2 shows the relationship between the temperature and time of polymer polymerization using DMA, N-Et-N-Meaniline and DEA as the promotors.

Please refer to FIG. 2. FIG. 2 shows the relationship between the temperature and time of polymer polymerization using DMA, N-Et-N-Meaniline and DEA as the promotors. It can be seen from the figure that when DMA and N-Et-N-Meaniline are used as the promotors, the temperature of polymerization reaction rises to 132-133° C., and the highest temperature is reached about 6.3 minutes after mixing. The results of this experiment show that when the amino groups on the promotor are two methyl groups or one methyl group and one ethyl group. The reaction rate and temperature are not affected. When the substituents are two ethyl groups, the maximum reaction temperature is 130° C. Though the results are similar to the previous experiment, the time to reach the maximum reaction temperature is extended to 11 minutes (almost two times). This result clearly shows that when the amino group on the promotor has a greater steric hindrance, the initial rate of polymerization can be slowed down.

Figure 3:
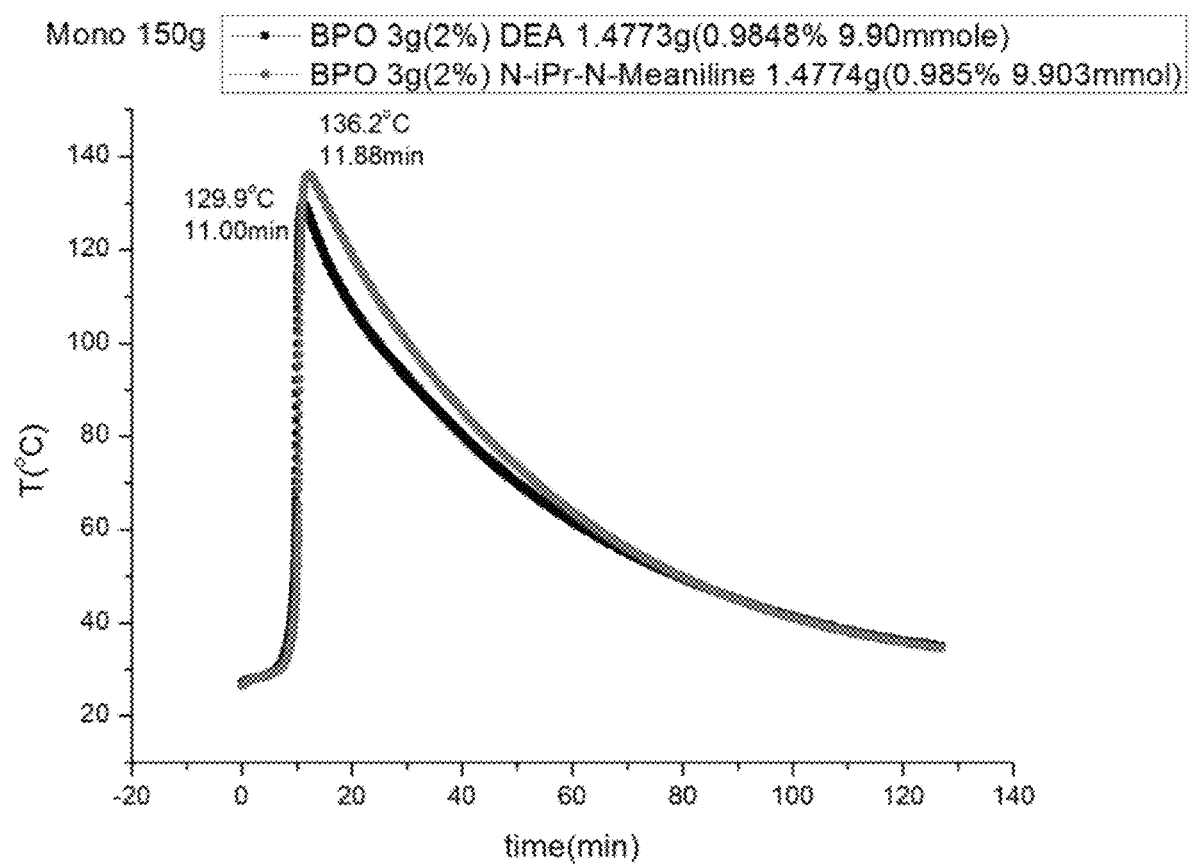
FIG. 3 shows the relationship between the temperature and time of polymer polymerization using DEA and N-iPr-N-Meaniline as the promotors.

Please refer to FIG. 3. FIG. 3 shows the relationship between the temperature and time of polymer polymerization using DEA and N-iPr-N-Meaniline as the promotors. Comparing the amino group on the promotor being two ethyl groups with the introduction of isopropyl group, the time to reach the maximum reaction temperature can be extended to 11.8 minutes. Although the time is further extended again, the time for the maximum reaction temperature has not been extended more, possibly because the other substituent is a methyl group and the steric hindrance is not increased too much. As a whole, the amino group on the promotor can affect the initial reaction rate.

Figure 4:
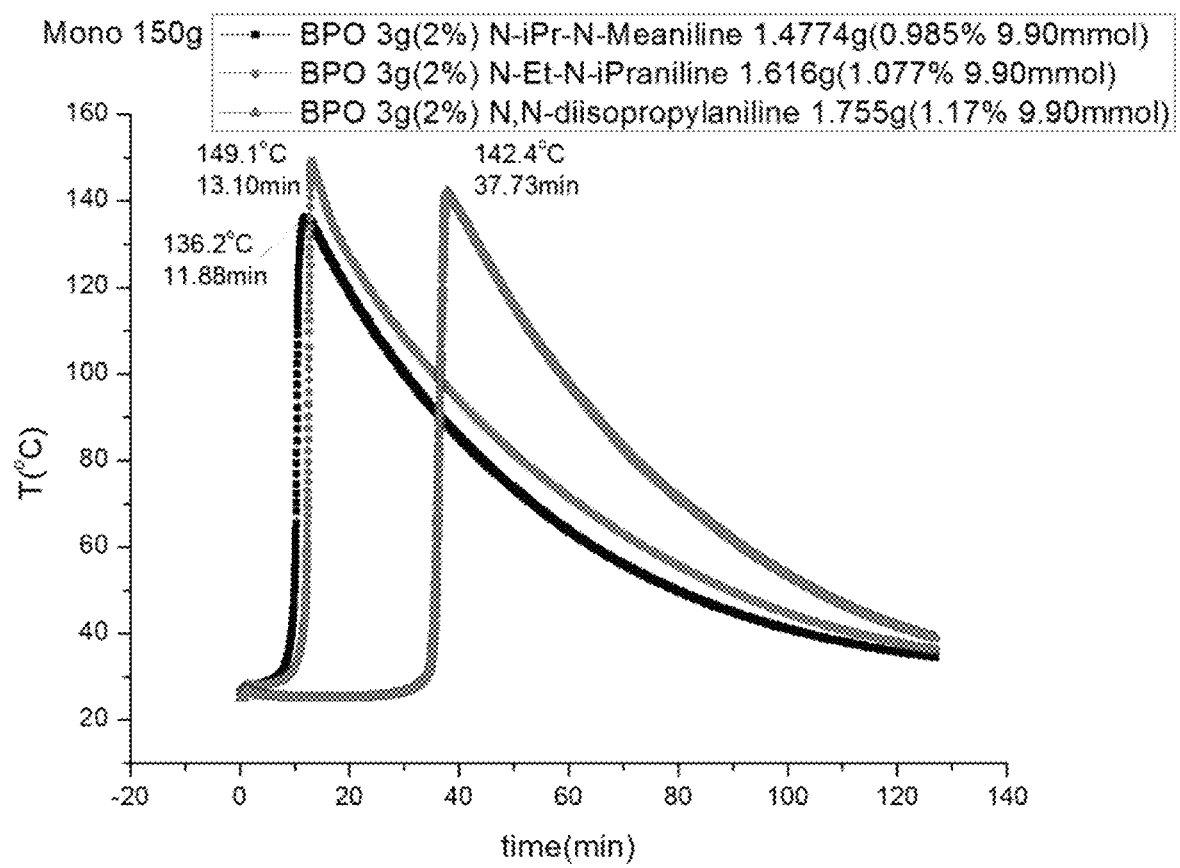
FIG. 4 shows the relationship between the temperature and time of polymer polymerization using N-iPr-N-Meaniline, N-Et-N-iPraniline and N,N-diisopropylaniline as the promotors.
Figure 5:
FIG. 5 shows the polymer polymerization sample using DMA as the promotor.
Figure 5:
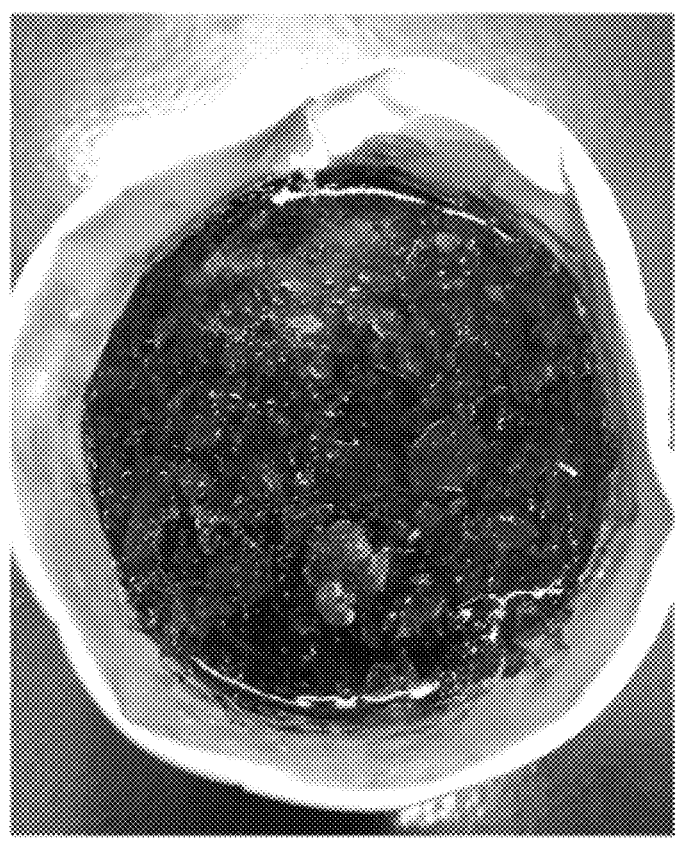
Figure 6:
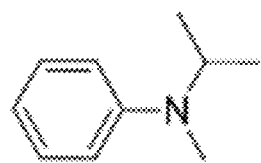
FIG. 6 shows the polymer polymerization sample using N-iPr-N-Meaniline as the promotor.
Figure 6:
Figure 7:
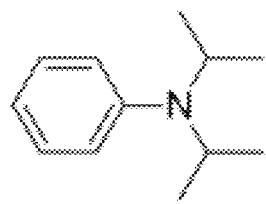
FIG. 7 shows the polymer polymerization sample using N,N-diisopropylaniline as the promotor.
Figure 7:

Please refer to FIG. 4, FIG. 5, FIG. 6 and FIG. 7. FIG. 4 shows the relationship between the temperature and time of polymer polymerization using N-iPr-N-Meaniline, N-Et-N-iPraniline and N,N-diisopropylaniline as the promotors. FIG. 5 shows the polymer polymerization sample using DMA as the promotor. FIG. 6 shows the polymer polymerization sample using N-iPr-N-Meaniline as the promotor. FIG. 7 shows the polymer polymerization sample using N,N-diisopropylaniline as the promotor. From FIG. 3 above, it can be seen that the time to reach the maximum reaction temperature can be extended when the amino group on the promotor is substituted by isopropyl group. Therefore, a substituent with bigger steric hindrance is further introduced to observe its impact on the time to reach the maximum reaction temperature. It can be seen from FIG. 4 that when N,N-diisopropylaniline is used as the promotor, the time to reach the maximum reaction temperature can be extended to 37.3 minutes. In addition to effectively extending the time to reach the maximum reaction temperature, it can be clearly seen from FIG. 5, FIG. 6 and FIG. 7 that the polymer is relatively free of white cracks when using the promotors with greater steric hindrance. This phenomenon is most likely due to the fact that the polymerization rate of the promotor with less steric hindrance is too fast such that hot spots are created, resulting in popcorn polymerization. Therefore, increasing the steric hindrance of the substituents on the amino group of the promotor can not only reduce the reaction rate, but also improve the polymerization quality of the polymer.

Among the foregoing, N,N-diisopropylaniline with the largest steric effect is the most effective. It can regulate and control the polymerization reaction rate and reaction temperature of vinyl ester with the BPO initiator, and also produces polymerization products perfectly under the correct equivalent.

The promotor of the present invention can reduce the cost, can be directly applied to the existing unsaturated polyester/vinyl ester market, and can also be applied to the special market targeting high thickness control demand.

The promotor of the present invention can control the thermosetting properties of the vinyl ester resin, and especially has a positive effect on time and/or temperature. This is controlled by the unique steric effect and electronic properties of the aniline derivative contained in the promotor, thereby achieving good polymerization of peroxides.

The novel promotor of the present invention can be used to regulate and control the free radical reaction mechanism. The whole curing reaction is expected to be controlled below 160° C. and the reaction time is expected to be no more than 100 minutes. The purpose of controlling the reaction temperature between 100° C. and 160° C. is that if it is lower than 100° C., the reaction will be incomplete, and if it is higher than 160° C., the workpiece will be overheated and deformed.

While the present disclosure has been described by means of specific embodiments, numerous modifications and variations could be made thereto by those skilled in the art without departing from the scope and spirit of the present disclosure set forth in the claims.

What is claimed is:

1. A method for preparing a promotor, wherein the promotor comprises an aniline derivative having the following structure:

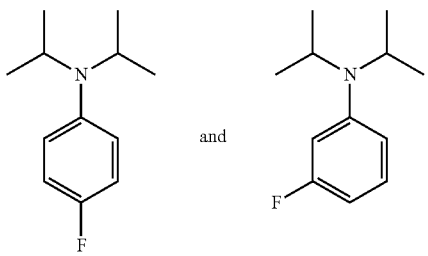

and the method comprises the following steps:

(a) pouring bromofluorobenzene and isopropylamine into a bottle and slowly adding potassium tert-butoxide to form a mixture;

(b) heating the mixture obtained in step (a) to reflux, and then filtering the mixture to remove potassium tert-butoxide after cooling to room temperature to obtain a first liquid;

(c) removing isopropylamine and tert-butanol from the first liquid obtained in step (b) by distillation under reduced pressure to form a second liquid; and (d) obtaining an organic phase from the second liquid obtained in step (c) by stratification, adding water into the organic phase for extraction and washing until the organic phase is not turbid, drying the organic phase with anhydrous magnesium sulfate and then filtering, removing excess solvent by concentration under reduced pressure, and finally removing excess reactant bromofluorobenzene from the concentrated organic phase by vacuum distillation to obtain the promotor.

* * * * *